US008618181B2

(12) United States Patent
Waguespack et al.

(10) Patent No.: US 8,618,181 B2
(45) Date of Patent: Dec. 31, 2013

(54) CHEMICAL PRODUCTION PROCESSES UTILIZING SYNGAS FROM PLASMA PYROLYSIS

(75) Inventors: James N. Waguespack, Deer Park, TX (US); James R. Butler, League City, TX (US)

(73) Assignee: Fina Technology, Inc., Houston, TX (US)

( * ) Notice: Subject to any disclaimer, the term of this patent is extended or adjusted under 35 U.S.C. 154(b) by 216 days.

(21) Appl. No.: 13/153,771

(22) Filed: Jun. 6, 2011

(65) Prior Publication Data

US 2011/0306684 A1    Dec. 15, 2011

Related U.S. Application Data

(60) Provisional application No. 61/354,296, filed on Jun. 14, 2010.

(51) Int. Cl.
*C07C 27/00*    (2006.01)

(52) U.S. Cl.
USPC .......................................... 518/700; 518/702

(58) Field of Classification Search
USPC ................................................. 518/700, 702
See application file for complete search history.

(56) References Cited

U.S. PATENT DOCUMENTS

2006/0185246 A1*    8/2006    Hanus et al. .................... 48/209

OTHER PUBLICATIONS

Patun et al (ACS Symposium Series (2007), 959(Ultraclean Transportation Fuels), 29-42).*

* cited by examiner

*Primary Examiner* — Jafar Parsa

(57) ABSTRACT

Chemical production processes are described herein. The chemical production processes generally include providing municipal solid waste; subjecting the municipal solid waste to plasma pyrolysis to form an intermediate for chemical production, wherein the intermediate includes carbon monoxide and hydrogen; and transferring the intermediate from the plasma pyrolysis to a chemical or liquid fuel production process.

16 Claims, No Drawings

CHEMICAL PRODUCTION PROCESSES UTILIZING SYNGAS FROM PLASMA PYROLYSIS

CROSS-REFERENCE TO RELATED APPLICATIONS

The present application claims priority to U.S. provisional patent application No. 61/354,296 filed on Jun. 14, 2010.

FIELD

Embodiments of the present invention generally relate to chemical production processes. In particular, embodiments relate to production of syngas via plasma pyrolysis and utilization of such syngas in chemical production processes.

BACKGROUND

Syngas is typically produced from processes, such as steam reforming of natural gas or liquid hydrocarbons or gasification of coal, for example. The syngas produced in large waste-to-energy gasification facilities can be used to generate electricity or as an intermediate in chemical production processes.

Recent research has been directed at more environmentally friendly processes for energy generation and/or chemical production. Efforts have been made to reduce the $CO_2$ footprint of such processes by utilizing renewable feedstocks, such as biology based feeds. While such feedstocks have had minimal success in energy generation processes, such have not generally been utilized in chemical processes.

Therefore, it is desirable to develop processes for chemical production whereby the $CO_2$ footprint is minimized while maintaining process conversion and efficiency.

SUMMARY

Embodiments of the present invention include chemical production processes. The chemical production processes generally include providing municipal solid waste; subjecting the municipal solid waste to plasma pyrolysis to form an intermediate for chemical production, wherein the intermediate includes carbon monoxide and hydrogen; and transferring the intermediate from the plasma pyrolysis to a chemical or liquid fuel production process.

One or more embodiments include the process of the preceding paragraph, wherein the intermediate comprises syngas.

One or more embodiments include the process of any preceding paragraph, wherein the chemical production process comprises a methanol production process.

One or more embodiments include the process of any preceding paragraph, wherein the chemical production process comprises a hydrogen production process.

One or more embodiments include the process of any preceding paragraph, wherein the chemical production process comprises an aromatics production process.

One or more embodiments include the process of any preceding paragraph, wherein the chemical production process comprises a liquid fuels production process.

DETAILED DESCRIPTION

Introduction and Definitions

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Syngas is a gas mixture containing varying amounts of carbon monoxide (CO), hydrogen and often, carbon dioxide ($CO_2$). Syngas is often utilized as a fuel source or as an intermediate for the production of other chemicals. Conventional methods of forming syngas include steam reforming of natural gas or liquid hydrocarbons and gasification of coal or biomass, for example.

However, the syngas utilized in embodiments of the invention is formed by green technologies. Such green technologies are capable of reducing the carbon footprint of syngas production (providing for the reuse of carbonaceous materials). In one or more embodiments, the syngas is formed from plasma pyrolysis of carbon containing biology-based (bio-based) materials. In one or more embodiments, the bio-based material is derived from biomass, such as lignin, corn, sugar cane, syrup, beet juice, molasses, cellulose, sorbitol, algae, glucose, acetates, such as ethyl acetate or methyl acetate or combinations thereof. As used herein, the term "biomass" excludes organic material which has been transformed by geological processes into substances, such as petroleum. In one or more embodiments, the bio-based material is derived from biogas, such as that produced by anaerobic digestion or fermentation of biodegradable materials, including biomass, manure, sewage, energy crops or combinations thereof, for example. As used herein, the term "biogas" refers to a gas produced by the biological breakdown of organic matter in the absence of oxygen.

In one or more specific embodiments, the bio-based material includes waste materials, such as municipal solid waste. Utilization of waste materials reduces the volume of waste entering landfills.

Syngas (or components thereof) may be formed from waste materials (identified as "C") as shown in the non-limiting reaction schemes illustrated below:

$C + H_2O \rightarrow CO + H_2$;

$C + O_2 \rightarrow CO_2$; and $CO_2 + C \rightarrow 2CO$.

Plasma pyrolysis generally includes gasification of a waste material, either in a furnace or reactor, with a plasma arc torch. The plasma arc torch may utilize gas, air or steam and powerful electrodes to form plasma (i.e., an ionized gas). Plasma pyrolysis generally utilizes temperatures as high as 10,000° F. to break molecular bonds through dissociation, creating basic atoms. Further, such high temperatures provide fusion of non-flammable inorganic components and their transformation to slag and metal components, which may be subsequently separated from the plasma through known technologies, such as floating separation, for example.

Use of plasma torches provides advantages over incinerators or other combustion processes because the intense heat generated by the plasma torch dissociates the waste material, causing the organic components of the waste to be turned to gas and causing the inorganic components of the waste to be converted to a relatively small volume of inert vitrified material without combustion or incineration. The gaseous stream consists primarily of hydrogen and carbon monoxide, the primary combustible components of syngas.

Occasionally, plasma pyrolysis includes the introduction of oxygen, which further promotes the formation of CO and $CO_2$. However, in processes utilizing little to no additional oxygen, the formed gas may include methane ($CH_4$), which may then be used directly in aromatics production processes, discussed in more detail below.

The syngas formed from the plasma pyrolysis process described herein may have a hydrogen to carbon monoxide ($H_2$:CO) molar ratio of from about 0.05:1 to about 3:1 or less than about 1:1, for example.

The syngas (or in certain embodiments, the methane) formed via plasma pyrolysis is utilized as a feed in chemical production processes, such as methanol, methane, hydrogen or aromatics production, or Fischer-Tropsch processes, for example.

Methanol production processes may include conversion of syngas to methanol as shown below:

$$CO_2 + 3H_2 \longleftrightarrow CH_3OH + H_2O;$$

$$H_2O + CO \longleftrightarrow CO_2 + H_2.$$

Such conversion may be accomplished by known processes, such as catalytic conversion, for example. Catalytic production of methanol from syngas is a high-temperature, high-pressure exothermic (heat generating) reaction. Catalysts useful in methanol production processes may include copper and/or zinc based catalysts, for example.

Hydrogen production processes for direct synthesis from syngas may include known processes, such as water-gas shift reactions to convert the syngas to hydrogen, such as via the following reaction scheme (including the addition of steam):

$$CO + H_2O \rightarrow CO_2 + H_2.$$

Separation processes are further contemplated to isolate/separate the hydrogen from the $CO_2$. Such separation processes may include pressure swing adsorption (PSA), amine scrubbing or membrane reactors, for example.

Fischer-Tropsch processes are chemical reactions that convert a mixture of carbon monoxide and hydrogen, such as syngas, into liquid hydrocarbons. The processes can produce a petroleum substitute for use as synthetic lubrication oil or synthetic fuels, for example.

The Fischer-Tropsch processes involve a variety of chemical reactions, which lead to a series of both desirable and undesirable byproducts. Useful reactions include alkane formation, diesel formation and gasoline formation. Alkane formation is illustrated by the following reaction scheme:

$$(2n+1)H_2 + nCO \rightarrow C_nH_{(2n+2)} + nH_2O.$$

In addition to alkane formation, competing reactions may result in the formation of alkenes, as well as alcohols and other oxygenated hydrocarbons.

Generally, the Fischer-Tropsch processes operate at a temperature of from about 150° C. to about 300° C. Higher temperatures lead to faster reactions and higher conversion rates but also tend to favor methane production. As a result, the temperature is usually maintained at the low to middle part of the range. Increasing the pressure leads to higher conversion rates and also favors formation of long-chained alkanes, both of which are desirable. Typical pressures range from one to several tens of atmospheres.

A variety of catalysts can be used for the Fischer-Tropsch process ("F-T"), but the most common are transition metal catalysts, such as those including cobalt, iron, nickel and ruthenium, for example. In addition to the active metal, the F-T catalysts may contain promoters, such as potassium or copper, for example. The F-T catalysts may further be supported on high-surface-area binders/supports, such as silica, alumina or zeolite, for example.

While the foregoing is directed to embodiments of the present invention, other and further embodiments of the invention may be devised without departing from the basic scope thereof and the scope thereof is determined by the claims that follow.

What is claimed is:

1. A chemical process comprising:
   providing municipal solid waste that does not comprise petroleum;
   subjecting the municipal solid waste to plasma pyrolysis to form an intermediate for chemical production, wherein the intermediate comprises carbon monoxide and hydrogen; and
   transferring the intermediate from the plasma pyrolysis to a chemical production process, wherein the chemical production process comprises a methanol production process, a hydrogen production process, or an aromatics production process.

2. The process of claim 1, wherein the intermediate comprises syngas.

3. The process of claim 1, wherein the chemical production process is the methanol production process.

4. The process of claim 1, wherein the chemical production process is the hydrogen production process.

5. The process of claim 1, wherein the chemical production process is the aromatics production process.

6. A chemical process comprising:
   providing a feedstock comprising a carbon containing biology based feed;
   subjecting the feedstock to plasma pyrolysis to form an intermediate for chemical production, wherein the intermediate comprises carbon monoxide and hydrogen; and
   transferring the intermediate from the plasma pyrolysis to a chemical production process, wherein the chemical production process comprises a methanol production process, a hydrogen production process, or an aromatics production process.

7. The process of claim 6, wherein the carbon containing biology based feed is derived from a biogas produced by anaerobic digestion or fermentation of manure, sewage, or combinations thereof.

8. The process of claim 6, wherein the intermediate comprises syngas having hydrogen to carbon monoxide molar ratio ranging from about 0.05:1 to about 3:1.

9. The process of claim 6, wherein the hydrogen to carbon monoxide molar ratio is less than about 1:1.

10. The process of claim 6, wherein the intermediate comprises syngas having hydrogen to carbon monoxide molar ratio that is less than about 1:1.

11. The process of claim 6, wherein the chemical production process is the methanol production process.

12. The process of claim 6, wherein the chemical production process is the hydrogen production process.

13. A chemical process comprising:
  providing a feedstock comprising a carbon containing biology based feed that is derived from a biogas produced by anaerobic digestion or fermentation of manure, sewage, or combinations thereof;
  subjecting the feedstock to plasma pyrolysis to form an intermediate for chemical production, wherein the intermediate comprises carbon monoxide and hydrogen; and
  transferring the intermediate from the plasma pyrolysis to a chemical production process or to a liquid fuel production process.

14. The process of claim 13, wherein the chemical production process comprises a methanol production process, a hydrogen production process, or an aromatics production process.

15. The process of claim 13, wherein the chemical production process is the methanol production process.

16. The process of claim 13, wherein the chemical production process is the hydrogen production process.

* * * * *